(12) United States Patent
McDonald et al.

(10) Patent No.: US 9,610,139 B2
(45) Date of Patent: Apr. 4, 2017

(54) DENTAL WEDGE

(71) Applicant: DENTSPLY INTERNATIONAL INC., York, PA (US)

(72) Inventors: Simon Paul McDonald, Katikati (NZ); Alejandro Aubone, Auckland (NZ)

(73) Assignee: DENTSPLY INTERNATIONAL Inc., York, PA (US)

( * ) Notice: Subject to any disclaimer, the term of this patent is extended or adjusted under 35 U.S.C. 154(b) by 164 days.

(21) Appl. No.: 14/120,299

(22) Filed: May 14, 2014

(65) Prior Publication Data

US 2014/0342311 A1 Nov. 20, 2014

(30) Foreign Application Priority Data

May 14, 2013 (NZ) ........................................ 610600

(51) Int. Cl.
*A61C 7/00* (2006.01)
*A61C 5/12* (2006.01)
*A61C 5/88* (2017.01)

(52) U.S. Cl.
CPC ................. *A61C 5/127* (2013.01); *A61C 5/88* (2017.02)

(58) Field of Classification Search
CPC ................................ A61C 5/127; A61C 15/02
USPC .................................................. 433/148, 149
See application file for complete search history.

(56) References Cited

U.S. PATENT DOCUMENTS

| 2,008,206 | A | | 7/1935 | Grant | |
|---|---|---|---|---|---|
| 3,193,094 | A | | 7/1965 | Schulstad | |
| 3,636,631 | A | * | 1/1972 | Tofflemire | A61C 5/127 433/149 |
| 3,890,714 | A | * | 6/1975 | Gores | A61C 5/127 433/149 |
| 4,337,041 | A | * | 6/1982 | Harsany | 433/149 |
| 4,449,933 | A | * | 5/1984 | Forni | 433/141 |
| 4,570,653 | A | | 2/1986 | Wolf | |
| 4,878,508 | A | | 11/1989 | Durbin | |
| 5,507,646 | A | | 4/1996 | Roth | |
| 5,775,346 | A | | 7/1998 | Szyszkowski | |
| 6,375,463 | B1 | * | 4/2002 | McLean et al. | 433/149 |

(Continued)

FOREIGN PATENT DOCUMENTS

CH 669514 A5 3/1989

OTHER PUBLICATIONS

International Search Report; PCT/US2014/000102; European Patent Office as International Searching Authority; Authorized Officer: Wirth, Christian; Date of Search: Aug. 14, 2014.

*Primary Examiner* — Heidi M Eide
(74) *Attorney, Agent, or Firm* — Leana Levin; Douglas J. Hura; David A. Zdurne

(57) ABSTRACT

A dental wedge, for use in the inter-proximal space between adjacent teeth, includes a head portion, a body portion, wherein, the body portion includes a backbone, wherein the backbone, viewed from the side, has a curved profile, the body portion includes at least three pairs of wings extending from the backbone, wherein the wings are separated by a plurality of notches such that the wings extend independently, and the body portion has three sections, wherein a proximal wing section includes a pair of wings closest to the head portion, a distal wing section includes a pair of wings furthest from the head portion, and a central wing section has at least one pair of wings, and a neck portion, wherein the neck portion connects the head and body portions.

18 Claims, 4 Drawing Sheets

(56) References Cited

U.S. PATENT DOCUMENTS

| | | |
|---|---|---|
| 6,468,080 B1 * | 10/2002 | Fischer et al. .............. 433/149 |
| 6,761,562 B2 | 7/2004 | Von Weissenfluh |
| 6,890,176 B2 | 5/2005 | Hahn |
| 2002/0055084 A1 | 5/2002 | Fischer et al. |
| 2003/0113688 A1 | 6/2003 | Weissenfluh |
| 2004/0014006 A1 | 1/2004 | Garrison et al. |
| 2005/0272005 A1 * | 12/2005 | Schaffner .............. A61C 5/127 433/149 |
| 2007/0254263 A1 * | 11/2007 | McDonald ................ 433/149 |
| 2008/0113315 A1 | 5/2008 | Beggs |
| 2011/0171596 A1 * | 7/2011 | Clark .......................... 433/149 |

* cited by examiner

DENTAL WEDGE

CROSS-REFERENCE TO RELATED APPLICATIONS

This application claims priority to New Zealand Application No. 610600, filed May 14, 2013, the entire contents of which is hereby incorporated by reference.

FIELD OF THE INVENTION

The present invention relates to an apparatus for use with dental matrixes during tooth restoration and in particular to dental wedges.

BACKGROUND OF THE INVENTION

To enable the dental professional to place composite fillings, matrixes are used. A matrix is a device which wraps around the tooth and acts as a mold to contain composite resins before they are cured. Matrices are generally formed of plastic or stainless steel and are either circumferential or sectional. Sectional matrices fit only in one proximal area of the tooth while circumferential matrix bands fit around the entire circumference of the tooth. Matrixes are secured in place by the use of wedges and/or clamps. The prior art wedges are generally made of wood or plastic and are placed between the matrix and an adjacent tooth. Wedges are used to hold the matrix against the tooth being filled and to temporarily separate the tooth being filled and the adjacent tooth. The dental wedge also serves as a gingival margin seal to apply pressure and control bleeding.

Most of the prior art dental wedges have a standard triangular shape. However, due to the irregular shape of the interproximal spaces, most standard shaped wedges are not always able to hold the matrix band against the prepared tooth to create a tight seal. Moreover, the convex shape of the matrix band opposes the flat surface of the wedge which decreases the contact surface area of a standard wedge against a matrix band. Thereby, a standard dental wedge cannot always seal the matrix band completely at the bottom of the preparation; nor can it achieve a large surface contact with the matrix band to provide more lateral support to improve adaptation. Examples of dental wedges are described in U.S. Pat. Nos. 8,425,228 and 8,206,151, both of which are hereby incorporated by reference in their entirety.

The dental wedge of the present invention aims to overcome the disadvantages of present dental wedges.

SUMMARY OF THE INVENTION

It is therefore an object of the present invention to provide a wedge for securing dental matrices which is an improvement on the prior art systems and devices or which will at least provide the industry with a useful choice.

It is an object of the present invention to provide a dental wedge that can provide a better adaptation than a standard wedge to the surface of the tooth and the shape of the interproximal area to seal the matrix band completely at the bottom of the preparation.

The present invention provides a dental wedge, for use in the inter-proximal space between adjacent teeth, said dental wedge comprising, a head portion, a body portion, wherein, said body portion includes a backbone, wherein said backbone, viewed from the side, has a curved profile, said body portion includes at least three pairs of wings extending from the backbone, wherein said wings are separated by a plurality of notches such that the wings extend independently, and said body portion has three sections, wherein a proximal wing section includes a pair of wings closest to the head portion, a distal wing section includes a pair of wings furthest from the head portion, and a central wing section has at least one pair of wings, and a neck portion, wherein said neck portion connects the head and body portions.

DETAILED DESCRIPTION OF THE PRESENT INVENTION

Figure 1:
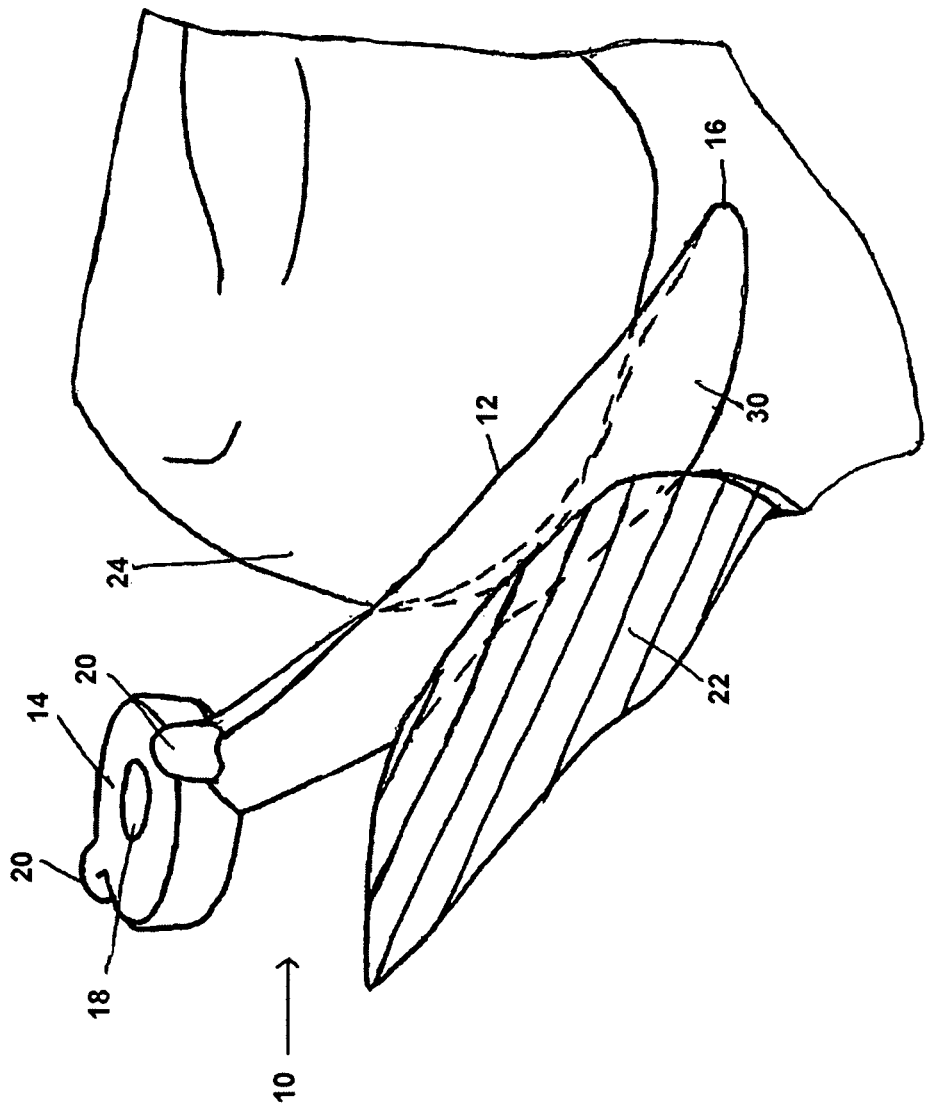
FIG. 1 is a view of a prior art dental wedge in use.

FIG. 1 illustrates use of a prior art wedge 10 in an interproximal space. The prior art wedge 10 includes a body 12 and handle 14. The body 12 includes a tapered end section extending to a tip 16. The handle 14 includes an opening 18. The wedge 10 includes one or more protrusions 20. After a matrix band (not shown) has been applied to a tooth 22, the wedge 10 is inserted between the matrix band and an adjacent tooth 24. The wedge 10 includes a handle that the dentist grasps to insert and remove the wedge 10. The wedge 10 is inserted in the buccal to lingual direction for teeth in the bottom part of the jaw (or buccal to palatal for the top part of the jaw) approximately along a longitudinal insertion axis.

Figure 2:
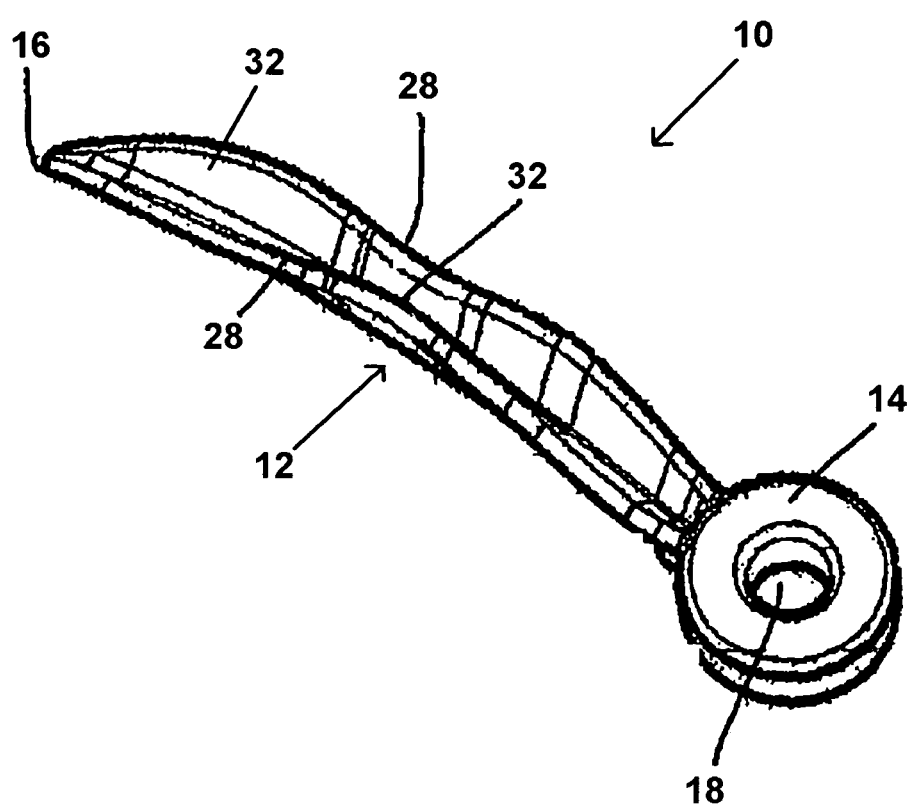
FIG. 2 is an orthogonal view from the bottom of a prior art dental wedge.

FIG. 2 illustrates the bottom view of the prior art wedge 10. The wedge 10 has a body 12. The body 12 is hollow on the bottom side, forming a hollow space and two opposing walls 28. The walls 28 each provide an outer wall portion 30 and an inner wall portion 32. When the wedge 10 is inserted in the interproximal space, the walls 28 may flex together into the hollow space. This flexing assists the wedge 10 in sealing the gingival margin of the matrix band. However, the walls 28 are made from one continuous segment of material, so the entire wall may experience flexing when pressure is applied to the central area of the walls 28. This is disadvantageous because it is less effective at sealing the gingival margin on the buccal and lingual sides of the matrix band. Furthermore, the walls 28 are directly attached to the handle. This is disadvantageous because the portion of the walls 28 near the handle resist flexing, thereby being less adaptable to the contours of the tooth.

Figure 3:
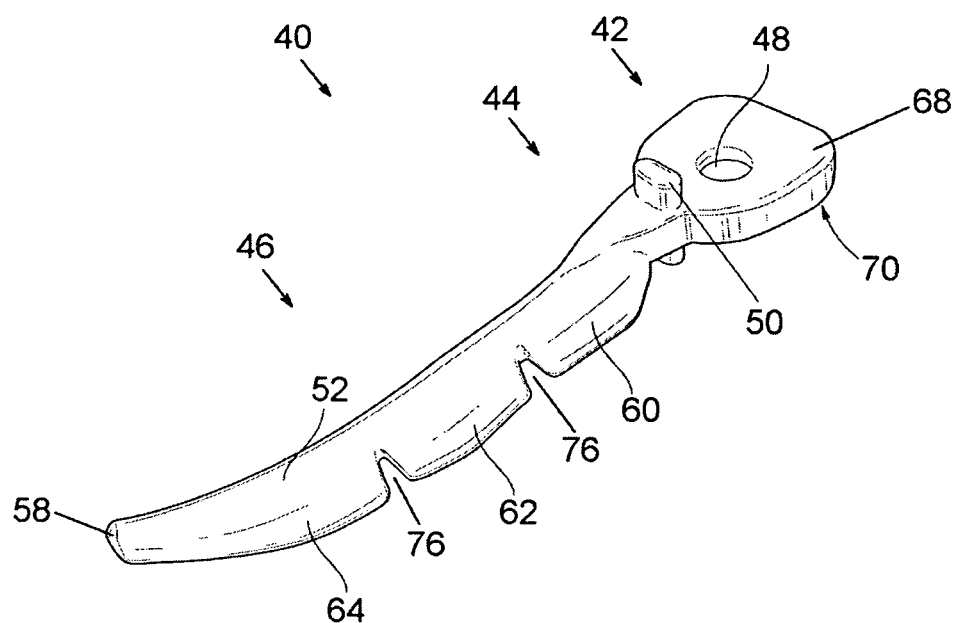
FIG. 3 is a perspective view of the dental wedge in accordance with the present invent ion.
Figure 4:
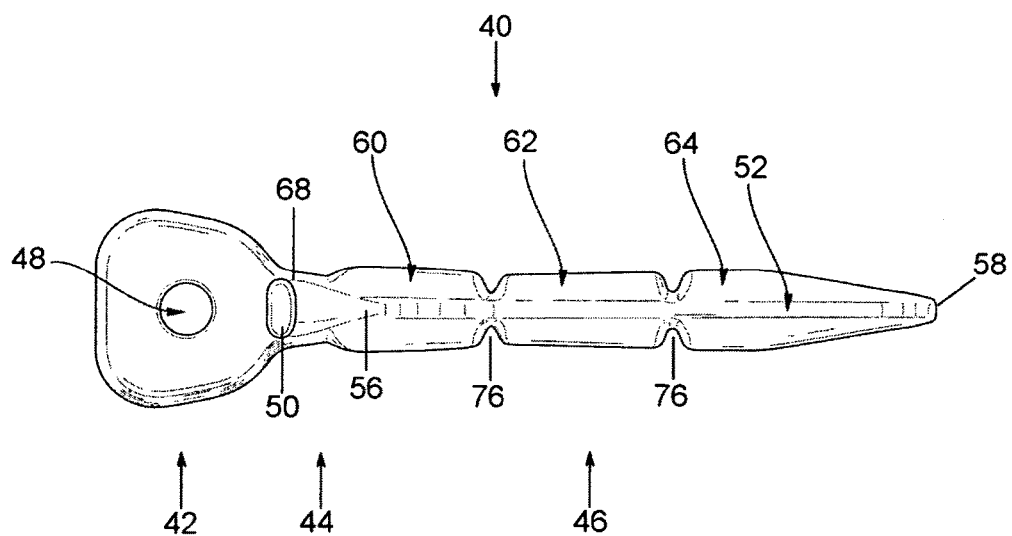
FIG. 4 is a top view of the dental wedge of the present invention as shown in FIG. 3.
Figure 5:
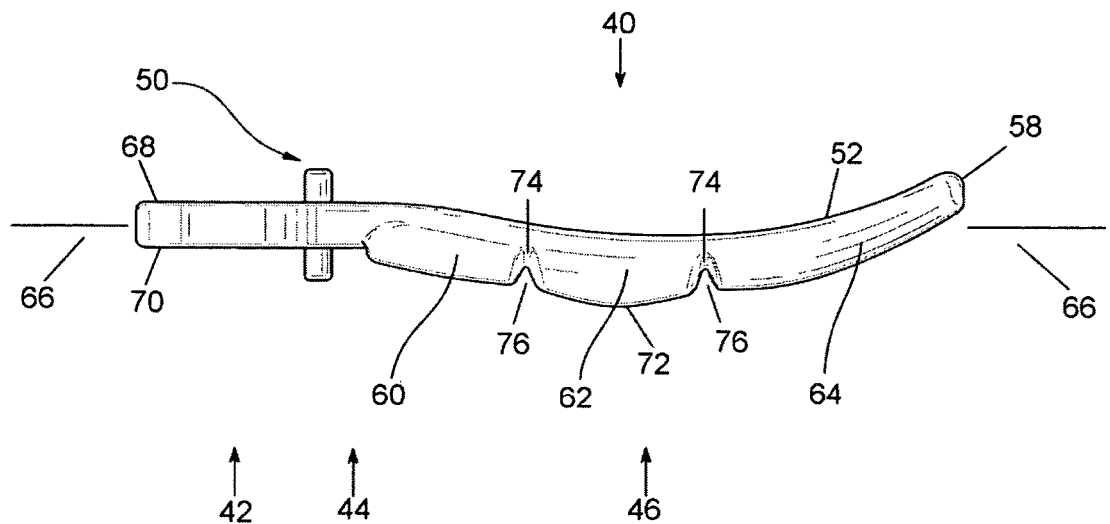
FIG. 5 is a side view of the dental wedge of the present invention as shown in FIG. 3.

The present invention, illustrated in FIG. 3-5, overcomes the disadvantages of the prior art by using a segmented design.

Referring to FIG. 4 the wedge 40 of the present invention comprises a one piece member of plastic and has three main parts, a head 42, a neck 44, and a body 46. As can be seen, the wedge 40 is shown to be symmetrical, in that the one side is a mirror image of the other side. The head 42 has a opening 48 therein. The opening 48 is adapted to accept a pair of pin-tweezers not illustrated. The head 42 also has a lug 50 that protrudes from the top and bottom surfaces 68, 70 of the head 42. The lug 50 serves as a grip for cotton tweezers during placement. The lug 50 is advantageous over prior art because its location on the head 42 allows greater flexibility of the body 46. Alternative embodiments (not shown) may include lugs 50 in other positions on the head 42 or neck 44, as well as multiple lugs 50. The wedge 40 has a backbone 52 that extends from the neck 44 and runs along the body 46. The neck 44 has a triangular shape where the base 54 of the triangle is attached to the bead portion and the tip 56 of the triangle portion continues to form the body's backbone 52. The sides of the neck 44 may slope inward as the next transitions from the head 42 to the backbone 52. The backbone 52 ends in a tip 58. The tip 58 is blunt to help prevent damage when the wedge 40 is inserted between teeth.

Three pairs of wings or wing sections 60, 62, 64 extend from the backbone 52. These wings 60, 62, 64 are separated by notches 76. As used herein, the term "notch" refers to a gap between two pieces of material, including but not limited to: cuts, slits, splits, openings, slots, and holes. The proximal wing section 60 is closest to the head 42 and terminates at the neck 44. This is advantageous over prior art because it enables the proximal wing section 60 to flex independently from the head 42. In another embodiment (not shown) an additional notch may separate the proximal wing section 60 from the neck 44. The distal wing section 64 is furthest from the head 42 and terminates at the tip 58. The distal wing section 64 tapers toward the tip 58, allowing easier insertion of the wedge 40 into the inter-proximal space. The central wing section 62 is located between the proximal wing section 60 and distal wing section 64. The central wing section 62 is narrower than the proximal wing section 60 and distal wing section 64 to allow the wedge 40 to better adapt to the contours of the tooth.

Referring to FIG. 5 the backbone 52 when viewed from the side has an asymmetrically curved concave profile. A longitudinal axis 66 runs through the head 42 along the length of the wedge 40. The tip 58 of the wedge 40 is higher than the head 42 compared to the longitudinal axis 66. The curvature of the backbone 52 allows the wedge 40 to sit deeper below the gingival margin of the preparation. Alternative embodiments (not shown) may include different degrees of curvature in the profile of the backbone 52. The lug 50 extends from both the top and bottom surfaces 68, 70 of the head 42 or at the margin between the head 42 and neck 44. Each wing is shown to include a bottom edge. The bottom edge of the central wing section 62 extends further from the backbone 52 than proximal wing section 60 and distal wing section 64. This extension forms a subtle apron 72 that provides additional support to a matrix band during deep cavity restoration.

In this embodiment, the notches 76 are notch-like separations in the wedge material between the proximal wing section 60 and central wing section 62 and between central wing section 62 and distal wing section 64. The notches 76 separate the material between the wing sections 60, 62, 64, allowing them to flex independently. In one embodiment, the notches 76 extend partially across the wings, leaving a connected portion 74 of the wings. In alternative embodiments, the notches 76 may extend all the way to the backbone 52, completely separating the wings and eliminating the connected portion 74. The individuality and flexibility of the wings help the wedge 40 better adapt to contours of the tooth and provide a greater seal with the matrix band because while one wing section is compressed, other wing sections may remain in a more expanded state.

FIG. 3 illustrates the present invention in a perspective view. The top and bottom surfaces 68, 70 of the opening 48 slope outward, forming an hourglass shaped opening 48 in the head 42. This shape enables a dentist to more easily guide pin tweezers into the opening 48 to grasp the wedge 40. Alternative embodiments may have different degrees of slope. This head 42 is thin enough to enable the arms of a pin tweezers to remain parallel when engaging the opening 48, thereby increasing grip of the wedge 40. Alternative embodiments may have heads of varying thicknesses.

The wedge 40 may be made in various sizes in alternative embodiments. The wedge 40 may be made of various materials including Santoprene™ thermoplastic vulcanizates from Advanced Elastomer Systems for a softer wedge, polypropylene for a harder wedge and polyethylene for a middle version. The wedge 40 may be made of clear plastic to allow light-activated resin to be cured by shining light through the wedge 40.

The invention claimed is:

1. A dental wedge, for use in the inter-proximal space between adjacent teeth, said dental wedge comprising:
 a head portion;
 a body portion, wherein,
 said body portion includes a backbone extending along the top of the body, wherein said backbone, viewed from the side, has a curved profile,
 said body portion includes at least three pairs of wings extending directly from the backbone and oriented generally longitudinally such that a cavity is formed between the wings of each pair wherein said wings are capable of flexing together and apart, and wherein said wings are separated by a plurality of notches such that the wings are capable of flexing substantially independently, and
 said body portion has three sections, wherein a proximal wing section includes a pair of wings closest to the head portion, a distal wing section includes a pair of wings furthest from the head portion, and a central wing section has at least one pair of wings; and
 a neck portion, wherein a proximal end of the neck portion connects the head portion and a distal end of the neck connects to the body portion and separates the backbone from the head portion and wherein the top surface of said neck portion tapers at the distal end and wherein the pair of wings closest to the head portion terminate in the neck portion.

2. The dental wedge as claimed in claim 1, wherein the curved profile of the backbone is asymmetrical, such that an end of the backbone opposite the head portion is higher than the head portion, whereby a portion of the wedge sits below a gingival margin of a tooth restoration preparation.

3. The dental wedge as claimed in claim 1, wherein the curved profile of the backbone is asymmetrical, such that an end of the backbone opposite the head portion is higher than an end of the backbone adjacent to the head portion, relative to a longitudinal axis extending through the head portion along a length of the body.

4. The dental wedge as claimed in claim 1, wherein one pair of wings in the central wing section extends from an apex of the curved profile of the backbone.

5. The dental wedge as claimed in claim 1, wherein at least one pair of wings in the central wing section is narrower when viewed from the top than the pairs of wings in the proximal and distal wing sections.

6. The dental wedge as claimed in claim 1, wherein the pairs of wings define a profile as viewed from the top, wherein the outside edges of the profile have a generally concave shape.

7. The dental wedge as claimed in claim 1, wherein at least one pair of wings in the central wing section extends further from the backbone than the pairs of wings in the proximal and distal wing sections.

8. The dental wedge as claimed in claim 1, wherein the pair of wings in the distal wing section furthest from the head defines a tip.

9. The dental wedge as claimed in claim 1, wherein the pair of wings in the distal wing section furthest from the head taper toward the backbone along a length of the body to form a spade shape.

10. The dental wedge as claimed in claim 1, wherein the notches completely separate the pairs of wings.

11. The dental wedge as claimed in claim 1, wherein the body has three pairs of wings.

12. The dental wedge as claimed in claim 1, wherein the dental wedge is made of plastic.

13. The dental wedge as claimed in claim 1, wherein the dental wedge is made of translucent material.

14. The dental wedge as claimed in claim 1, wherein the curved profile of the backbone presents a concave curved profile.

15. The dental wedge as claimed in claim 1, wherein the head portion, the neck portion, or the head portion and the neck portion includes one or more lugs extending from the wedge, whereby the dental wedge may be grasped with a medical tool.

16. The dental wedge as claimed in claim 1, wherein the head portion includes an opening, whereby the dental wedge may be grasped with a medical tool.

17. The dental wedge as claimed in claim 1, wherein the wings are partially separated by the notches, such that the wings have a connected portion.

18. A dental wedge, comprising:

a head portion located at a proximal end of the device;

a body portion extending distally from the head, the body portion having a backbone extending along the top of the device and terminating in a distal tip, a plurality of flexible wings extending directly from the backbone, the wings being generally oriented along the length of the backbone in pairs, the wings of each pair extending outward from the backbone, and a plurality of notches separating the wings of each pair from the wings of adjacent pairs, such that the wings of each pair are capable of flexing substantially independently from the wings of adjacent pairs; and a neck portion extending between the head and the backbone, the neck portion having a generally triangular shape wherein a base portion of the triangle abuts the head and a tip portion of the triangle narrows to approximately width of the backbone, such that a smooth transition is formed between the neck and the backbone, the neck portion separating a proximal-most pair of wings from the head portion.

* * * * *